United States Patent
Esmailzadeh

[19]

[11] Patent Number: 5,873,363
[45] Date of Patent: Feb. 23, 1999

[54] METHOD AND APPARATUS FOR BREATHING

[76] Inventor: Karim Esmailzadeh, 3905 Viola Rd. NE., Rochester, Minn. 55906

[21] Appl. No.: 660,743

[22] Filed: Jun. 6, 1996

[51] Int. Cl.[6] .................................................. A61F 5/56
[52] U.S. Cl. ..................................... 128/207.18; 128/848
[58] Field of Search ........................ 128/200.15, 200.28, 128/201.26, 205.25, 206.12, 206.13, 206.14, 206.19, 206.21, 206.29, 207.11, 206.25, 204.17, 204.11, 848, 857

[56] References Cited

U.S. PATENT DOCUMENTS

| 1,216,679 | 2/1917 | Foster | 128/848 |
|---|---|---|---|
| 1,354,652 | 10/1920 | Jefferies | 128/206.25 |
| 1,519,915 | 12/1924 | Johnson | 128/848 |
| 1,629,892 | 5/1927 | Storms | 128/848 |
| 5,265,280 | 11/1993 | Walsh | 128/206.19 |
| 5,316,020 | 5/1994 | Truffer | 128/848 |
| 5,462,066 | 10/1995 | Snyder | 128/848 |

OTHER PUBLICATIONS

Colin E. Sullivan and Michael Berthon–Jones, Reversal of Obstructive Sleep Apnoea By Continuous Positive Airway Pressure Applied Through the Nares, The Lancet, pp. 862–865, Apr. 18, 1981.

John W. Shepard, *Hypertension, Cardiac Arrhythmias, Myocardial Infarction, and Stroke In Relation to Obstructive Sleep Apnea,* Mayo Medical School, vol. 13, No. 2, pp. 437–438, Sep. 1992.

John W. Shepard, Jr., et al., *Evaluation of the Upper Airway in Patients with Obstructive Sleep Apnea,* Sleep, vol. 14, No. 4, pp. 361–371, 1991.

James M. Parish and John W. Shepard, Jr., *Cardiovascular Effects of Sleep Disorders,* Chest, vol. 97, pp. 1220–1226, May 1990.

*Primary Examiner*—V. Millin
*Assistant Examiner*—William J. Deane, Jr.
*Attorney, Agent, or Firm*—Mackall, Crounse & Moore, PLC

[57] ABSTRACT

The present invention is an apparatus and method for urging proper breathing. The apparatus comprises an oral barrier placed in or over the mouth having an air impervious layer to prevent airflow into the mouth and through an oral air passageway. The oral barrier may also have an appendage extending into the mouth to engage the tongue and teeth. The apparatus may also comprise a mouth closer urging the mouth into the closed position to prevent the entry of air through the mouth and into the oral passageway. The mouth closer further secures the tongue in the mouth.

8 Claims, 3 Drawing Sheets

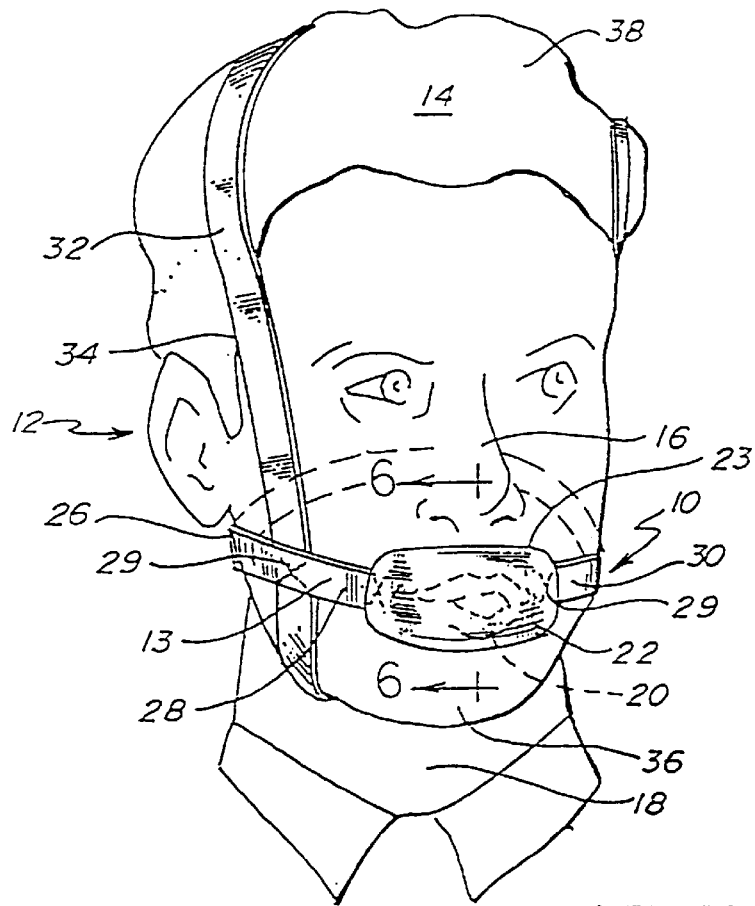
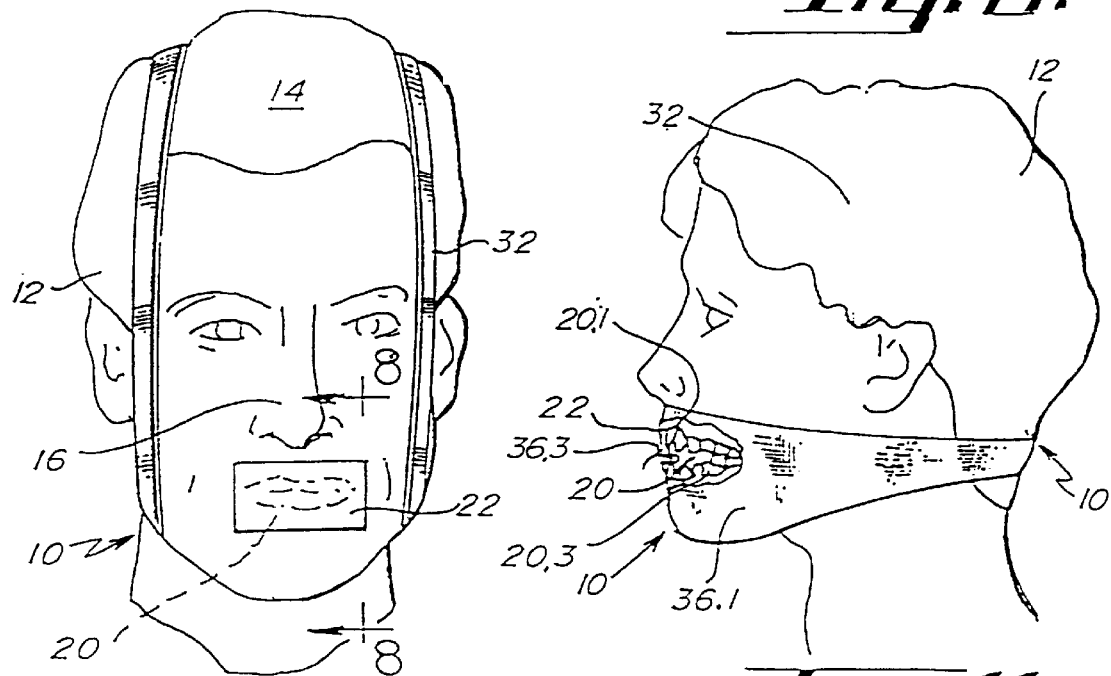

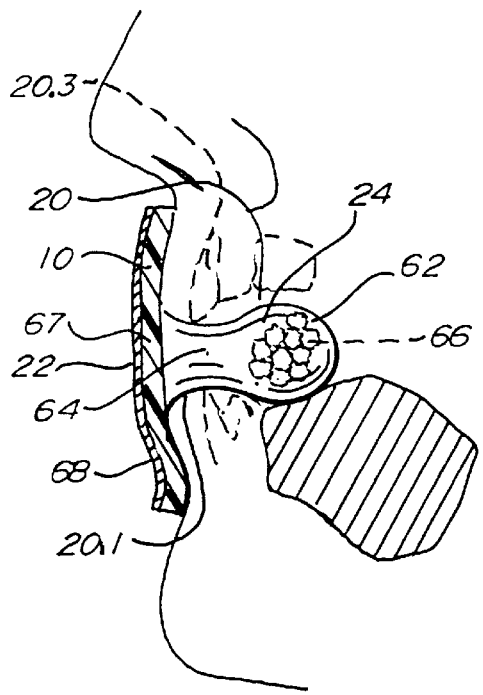
_Fig. 6._
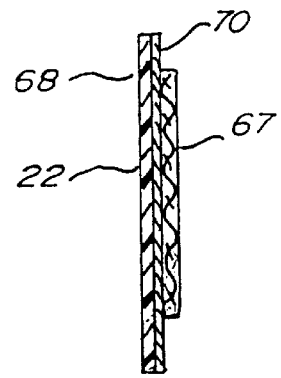
_Fig. 8._
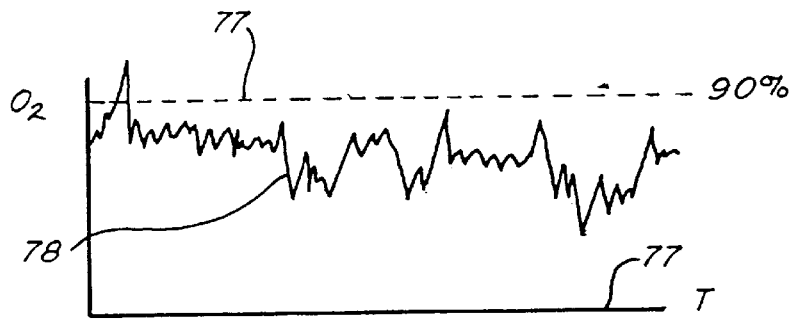
_Fig. 9._
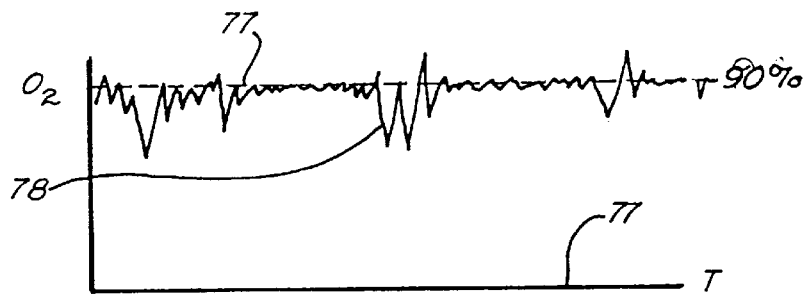
_Fig. 10._

METHOD AND APPARATUS FOR BREATHING

BACKGROUND OF THE INVENTION

The present invention relates to a method and apparatus for breathing. Breathing improperly is known to cause problems due to a body receiving an inadequate quantity of oxygen causing physiological effects. For example, failure to breathe properly during sleep is known to cause a person to indicate symptoms of sleepiness during waking hours, fatigue and reduced health.

While sleeping the problem known as obstructive sleep apnoea is a common disorder, particularly in middle age people. The problem is a sleep-induced blockage of the airway which results in apnoeic episodes during sleep. The sleep is fragmented causing continuing degeneration over months or years. This continuing degeneration worsens the problem with the apnoeic episode frequently exceeding two minutes in a sleeper and causing the blood/oxygen saturation level to fall below 90%.

As a person sleeps, the nasal air passageway from the nose to the lungs may become partially blocked or interrupted by tissues, such as the tongue, in the throat and mouth area. The obstruction of the airway causes a degree of asphyxia in the sleeper due to reduced oxygen being absorbed into the body. This obstruction may cause the sleeper to wake frequently during the sleeping time to breath, resulting in insufficient rest. Major symptoms of the sleep apnoea problem are excessive daytime sleepiness and snoring. The daytime sleepiness is due to the problem preventing a sleeper from getting sufficient rest while sleeping. Snoring may be associated with this obstruction as an indication of blockage of the airway leading to the lungs. The partial asphyxia may cause a variety of problems in the sleeper including hypertension, heart problems, headaches, and personality changes.

The obstructive sleep apnoea has also been linked to stroke mortality, myocardial infarction and sudden cardiac death. More than 75% of patients with obstructive sleep apnoea have been reported having a variation in heart rate referred to as Brady tachy-arrhythmia. Studies have shown that the heart rate slows with the cessation of ventilation during obstructive sleep apnoea and the extent of slowing correlates to the duration and amount of oxygen desaturation caused by the problem. The heart rate increases suddenly as the sleeper wakes and the obstructive apnoea is terminated. This variation in heart rate has been shown to reduce the amount of oxygen distributed to the body. The combination of reduced heart rate and reduced oxygen distribution have been linked to the problems of myocardial infarction, sudden death and stroke.

The problem of obstructive sleep apnoea may be caused by reduced pressure in the body airway during inspiration which urges the tongue and soft palate to block the body airway. There has also been evidence that failure of muscles in the throat may further allow blockage of the body airway. Furthermore, the suction created by a sleeper having airway resistance in the mouth or nose region may cause additional pressure causing the body airway to collapse. Gravity may also force the mouth into an open position allowing the tongue, soft palate and pharynx to block the body airway (FIG. 2).

Surgically opening the airway at the throat of the sleeper and the use of a pneumatic pressurizing system have been tried to prevent blockage of the airway and allow a sleeper sufficient airflow into the lungs to prevent these problems. The pneumatic pressurizing system (FIG. 3) has been used to provide a continuous positive body airway pressure acting as a pneumatic splint in holding the body airway in communication with a pressurizing device which supplies air to the nasal air passageway. Surgically opening the airway through a tracheostomy is left open at night and is affective at relieving the obstructive sleep apnoea. Both of these previously tried solutions are expensive and difficult to tolerate.

Improper breathing can also be a health problem during exercise or other activity during the non-sleeping hours. By breathing through the mouth, phlegm is allowed to buildup in the nose and upper throat. Furthermore, the tongue, soft palate, or other soft tissues may block the oral air passageway allowing an insufficient amount of air into the body airway. This blockage may result in reduced oxygen levels in the blood and associated drowsiness or other health problems. The present invention is designed to alleviate these problems with a sleeper while avoiding the cost and complications of the previously tried solutions.

SUMMARY OF THE INVENTION

The present invention is an apparatus and method for aiding an air breathing animal, such as a person, to breath properly during resting, exercise or other daytime activities. The apparatus comprises an oral barrier placed in or over the mouth to prevent airflow into the mouth and through an oral air passageway. The oral barrier may also have an appendage extending into the mouth to engage the tongue and teeth. The apparatus may also comprise a mouth closer bearing against the jaw to urge the mouth closed to prevent the entry of air through the mouth and into the oral passageway. The mouth closer may also help secure the tongue in the mouth. The apparatus may be attached over the mouth by a resilient strap encircling the head or by other means.

A feature of the present invention is an air impervious fabric material in the oral barrier to prevent air from passing through the oral barrier.

Another feature of the present invention is a mouth closer extending from the top of the head to under the chin of the sleeper to urge the mouth into a closed position.

An advantage of the present invention is it is easy and inexpensive to manufacture.

Another advantage of the present invention is that it is small and easy to carry or pack in typical luggage compartments.

Another advantage of the present invention is it is easily removable.

Another advantage of the present invention is that it is washable and reusable.

Another advantage of the present invention is it may be used for the prevention of sleep apnea.

Another advantage of the present invention is the oral barrier may be worn by a person while exercising to facilitate breathing through the nose.

An object of the present invention is to provide an inexpensive device to relieve the symptoms of sleep disorders related to breathing problems associated with blockage of the airway.

Another object of the present invention is to provide a reusable device which may be cleaned in a regular laundry cleaning apparatus.

Another object of the present invention is to provide a device which, through its use, closes the mouth to urge breathing through the nose.

3

BRIEF DESCRIPTION OF THE DRAWINGS

FIG. 5 is a perspective view of a person in outline wearing the present invention.

FIG. 6 is a detail section view taken at approximately 6—6 of FIG. 5.

FIG. 7 is a front elevational view of a sleeper wearing an alternative embodiment of the present invention.

FIG. 8 is a detail section view taken at approximately 8—8 of FIG. 7.

FIG. 9 is a chart showing the oxygen level in the sleeper without using the device.

FIG. 10 is a chart showing the oxygen level in the sleeper wearing the device.

FIG. 11 is a side elevational view of a person wearing an alternative embodiment of the present invention.

DETAILED DESCRIPTION OF THE PREFERRED EMBODIMENTS

Figure 1:
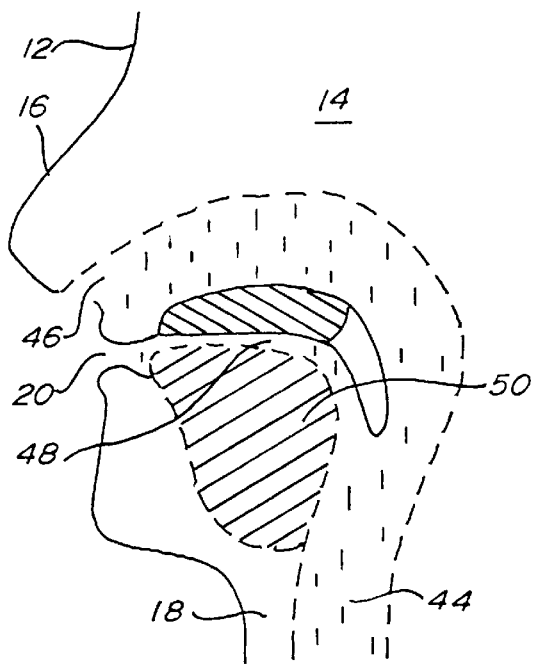
FIG. 1 is a section view of a person showing the body airway opening to the nose and mouth.

Referring to FIG. 1, a person 12 is shown having a head 14, a nose 16, a neck 18 and a mouth 20. The person 12 has a body airway 44 for receiving air from a nasal air passageway 46 or an oral air passageway 48. As shown in FIG. 1, the nasal air passageway 46 and the oral air passageway 48 are in communication with the body airway 44. The oral air passageway 48 is in communication with the mouth 20. The nasal air passageway 46 is in communication with the nose 16. The body airway 44 extends from the head 14 through the neck 18 along the throat 42. The oral air passageway 48 joins the nasal air passageway 46 near the back of the tongue 50 to provide air to the lungs (not shown) through the body airway 44.

Figure 2:
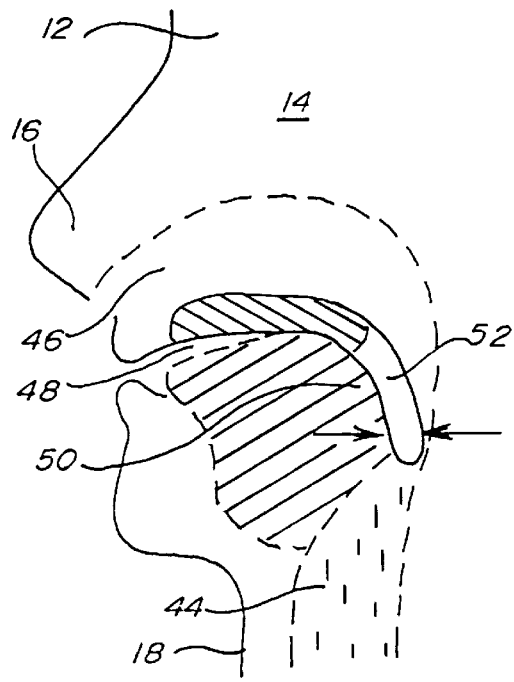
FIG. 2 is a section view showing the tongue and soft palate blocking the body air way.

Referring to FIG. 2, the tongue 50 and the soft palate 52 may be urged away from the mouth 20 by gravity or suction in the body airway 44. The movement of the soft palate 52 and the tongue 50 may block the air passageway 44 preventing air from entering the body at the nasal air passageway 46 or the oral passageway 48.

Figure 3:
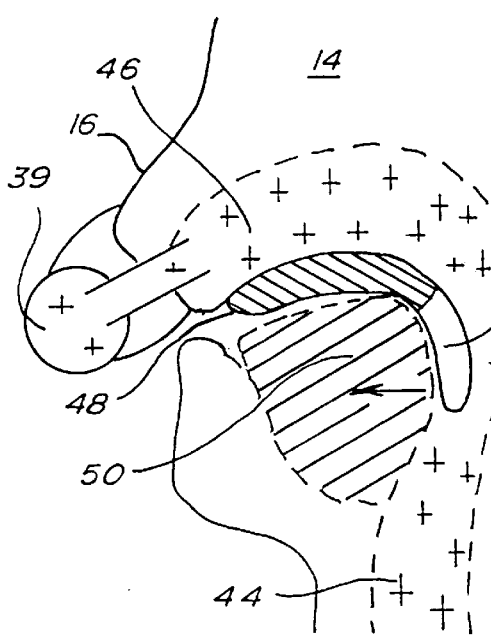
FIG. 3 is a section view showing a prior art device.

Referring to FIG. 3, a prior art device 39 is shown attached to the nose 16 for pressurizing the nasal air passageway 46. This pressurizing device 39 may be similar to devices available from Respironics, Inc. of Murrysville, Pa. This device is shown applying pressure to the nasal air passageway forcing the soft palate 52 to bear against the back of the tongue 50 and creating a pressurized condition in the body airway 44. As shown in FIG. 3, the pressurizing device 39 is bulky and uncomfortable.

Figure 4:
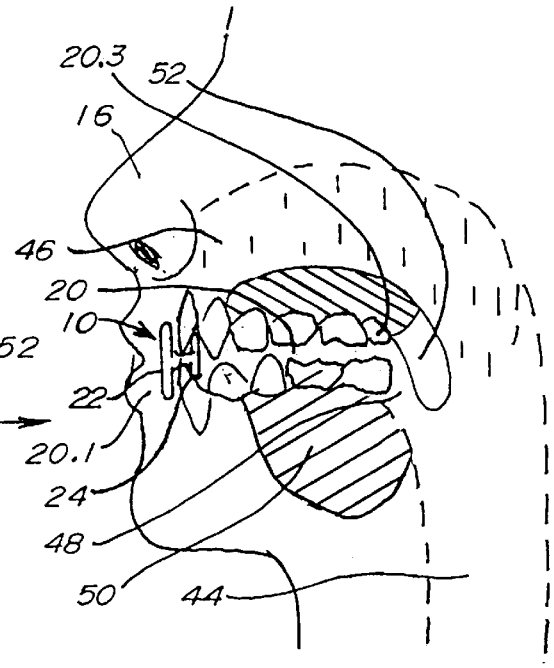
FIG. 4 is a section view showing the present invention in the mouth blocking the oral air passageway.

Referring to FIG. 4, the sleeping device 10 is shown blocking the oral air passageway 48 to urge air to enter the nose 16 and pass through the nasal air passageway 46. The sleeping device 10, shown in FIG. 4, comprises an oral barrier 22 in the mouth 20 between the teeth 20.3 and the lips 20.1. The oral barrier 22 may have an appendage 24 extending into the mouth 20. The sleeping device 10 blocks the oral air passageway 48 forcing air into the nasal air passageway 46. Air passing through the nasal air passageway may reduce phlegm (not shown) generated in the nose which may cause additional blockage of the body airway 44.

4

Referring to FIG. 5, the sleeping device 10 is shown affixed over the mouth 20 and held in place by a removable fastener 13 illustrated as an oral barrier strap 26. The sleeping device 10 comprises an oral barrier 22 over the mouth 20. The oral barrier 22 has a size sufficient to cover the mouth 20 while not covering the nose 16. The oral barrier 22 may have a contoured outside edge 23 to accommodate the nose 16.

Continuing to refer to FIG. 5, the oral barrier strap 26 is made from a resilient material 28 attached to the oral barrier 22. The oral barrier strap 26 also has a second end 30 attached to the oral barrier in a position spaced from the first end 28 on the oral barrier to removably hold the oral barrier in place over the mouth such as a patch. Stitching 29 is used to secure the first end 28 and the second end 30 to the oral barrier.

Continuing to refer to FIG. 5, the sleeping device 10 may also comprise a mouth closer 32. The mouth closer 32 may comprise a chin strap 34 extending under the chin 36 on the head 14 of the person 12. The chin strap 34 may also extends over the top 38 of the head 14 and is made of a resilient material to bear against the chin 36 to urge the mouth 20 to close. The chin strap 34 and the oral barrier strap 26 may be connected by stitching 29 to prevent slipping on the sleeper's head 14.

Referring to FIG. 6, the sleeping device 10 is shown with the appendage 24 protruding into the mouth 20. The appendage 24 may have a pacifier end 62 and a soft body 64 which may be filled with a soft filler material 66 such as sponge, gauze or other pliable material. The oral barrier 22 may have a fabric layer 68 which is impervious to air to prevent air from entering the mouth 20 when the sleeping device 10 is in place. The oral barrier 22 may also have an outside layer 67 sealing bearing against the head 14 and formed of a synthetic material for comfort against the mouth 20 and to resist contamination from germs.

Referring to FIG. 7, the sleeping device 10 is shown in an alternative embodiment having a oral barrier 22 removably mounted over the mouth 20. The oral barrier 22 may be separate from the mouth closer 32.

Referring to FIG. 8, the oral barrier 22 is shown having the air impervious layer 68 and the outside layer 67. An adhesive 70 is placed on the oral barrier 22 to removably attach the oral barrier to the head for covering the mouth.

Referring to FIG. 9, the oxygen level 77 may be measured during the period 78 of sleep. As the sleep duration increases, the body oxygen level decreases below 90% causing the sleeper to wake to take a breath. These waking moments are illustrated by the spikes and oxygen level with respect to time. The oxygen level in the sleeper steadily declines during the period of sleep 78 due to the obstructive sleep apnoea.

Referring to FIG. 10, the oxygen level, when measured on a sleeper wearing the breathing device 10 is shown having greater consistency during the period 78 of sleep.

Referring to FIG. 11, the sleeping device 10 may comprise a ribbon 36.1 of resilient material extending around the back of the head 14 of the sleeper 12. The ribbon 36.1 of resilient material may have an oral barrier 22 as illustrated in FIG. 4, inserted into the mouth 20 of the sleeper 12, in this embodiment the oral barrier 22 is positioned between the lips 20.1 and the teeth 20.3. The mouth 20 is closed by a reflex action of the sleeper 12. The oral barrier 22 in the embodiment shown in FIG. 11 is a multilayer construction similar to the illustration in FIG. 6. The oral barrier 22 is attached by a string 36.3 or similar device extending to the ribbon 36.1 of resilient material to retain the oral barrier 22 spaced from the throat 42. The oral barrier 22 is retained by the lips 20.1

In operation, the oral barrier 22 is placed in the oral air passageway which extends from the lip 20.1 through the mouth 20 to the body airway 44. The oral barrier 22 is positioned to block the oral air passageway 48 and urge air to enter the nasal air passageway 46 during breathing. The oral barrier 22 may be held in place by an oral barrier strap 26, a ribbon 36.1 of material extending around the head 14, and adhesive 70, or by engagement with the lips 20.1 and the teeth 20.3. The appendage 24 may also align the oral barrier 22 with the oral air passageway 48. The oral barrier 22 should be affixed over the oral air passageway 48 for easy removal.

Referring to FIG. 5, the mouth closer 32 is mounted on the head 14 bearing against the chin 36 to urge the mouth 20 closed. The person 12 then assumes a sleeping position and relaxes.

The oral barrier 22 prevents air from entering the mouth 20 which also causes a reflex action in the person 12 to naturally close the mouth 20. The use of the mouth closer 32 further urges the mouth 20 to close.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A method of improving breathing by a person using an oral barrier, the person having a head having a mouth and a nose, an oral air passageway in communication with a mouth, a nasal air passageway in communication with a nose, the method comprising:

placing an oral barrier in communication with an oral air passageway, the oral barrier positioned to block the oral air passageway;

securing the oral air barrier in a mouth by means of an appendage having a pacifier end and a soft body filled with a soft filler material;

closing a mouth of a person whereby air is prevented from entering an oral air passageway urging the person to breathe through the nasal air passageway.

2. The method of claim 1 further comprising the step of affixing the oral barrier over an oral air passageway.

3. The method of claim 1 further comprising a step of urging the mouth to a closed position.

4. The method of claim 3 wherein the step of urging further comprises the step of placing a mouth closer on a head of a person wherein the mouth closer bears against a jaw in a head to urge a mouth into the closed position.

5. An apparatus for use with a head having a mouth in communication with an oral air passageway and a nose in communication with a nasal air passageway, a mouth having a closed position, the apparatus comprising:

an oral barrier having a size and an air impervious layer in the mouth, the air impervious layer removably held in place blocking the oral air passageway; and an appendage on a oral barrier, the appendage protruding into the mouth, the appendage further comprising a pacifier end and a soft body filled with a soft filler material.

6. The invention of claim 5 wherein a head has a chin, a apparatus further comprising a mouth closer on a head bearing against a chin to urge the mouth into a closed position.

7. The invention of claim 5 further comprising a ribbon of material attached to the oral barrier, a ribbon of material extending around the head.

8. The invention of claim 6, a mouth closer further comprising a chin strap on the head, a chin strap extending around a head and around the chin to urge the mouth to close.

* * * * *